United States Patent

Katoh et al.

[11] Patent Number: 6,140,537
[45] Date of Patent: Oct. 31, 2000

[54] PROCESS FOR PRODUCING BORON COMPOUNDS

[75] Inventors: Tsuyoshi Katoh; Morihiko Yamada, both of Kanagawa, Japan

[73] Assignee: Showa Denko K.K., Tokyo, Japan

[21] Appl. No.: 09/367,130

[22] PCT Filed: Feb. 5, 1998

[86] PCT No.: PCT/JP98/00477

§ 371 Date: Aug. 5, 1999

§ 102(e) Date: Aug. 5, 1999

[87] PCT Pub. No.: WO98/34938

PCT Pub. Date: Aug. 13, 1998

[30] Foreign Application Priority Data

Feb. 6, 1997 [JP] Japan ..................... 9-023930

[51] Int. Cl.$^7$ .................................. C07F 5/02
[52] U.S. Cl. ................... 564/8; 546/13; 568/6; 568/2; 568/1
[58] Field of Search ............ 568/1, 2, 6; 564/8; 546/13

[56] References Cited

U.S. PATENT DOCUMENTS

| | | | |
|---|---|---|---|
| 4,613,373 | 9/1986 | Umeno et al. | 106/18.3 |
| 4,900,854 | 2/1990 | Winterton et al. | 556/70 |
| 5,053,537 | 10/1991 | Gitzel et al. | 564/8 |
| 5,055,619 | 10/1991 | Gitzel et al. | 568/2 |
| 5,932,393 | 8/1999 | Cunningham et al. | 430/281.1 |
| 6,002,044 | 12/1999 | Yamada et al. | 564/8 |
| 6,011,180 | 1/2000 | Cunningham et al. | 568/6 |

*Primary Examiner*—Jeremy Richli
*Assistant Examiner*—Jean F Vollano
*Attorney, Agent, or Firm*—Sughrue, Mion, Zinn, Macpeak & Seas, PLLC

[57] ABSTRACT

A method of producing a boron-based compound represented by general formula (1) including a first step of reacting lithium, magnesium or a compound containing lithium, a compound represented by general formula (2), and a compound represented by general formula (3): $R^2$—Y to produce a borate metal salt represented by general formula (4), and a second step of adding to the borate metal salt an onium halide represented by general formula (5): $Z^+ \cdot X^-$ to effect ion exchange reaction (the symbols in the formulae have the same meanings as described in the specification).

According to the production method of the present invention, a high purity boron-based compound represented by the general formula (1) above useful as a photopolymerization initiator and a light-absorbing decolorizing agent can be obtained in a short time and a high yield as compared with the conventional method.

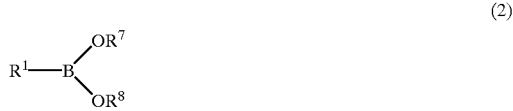

(2)

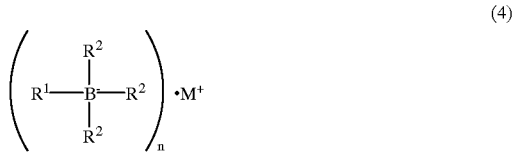

(4)

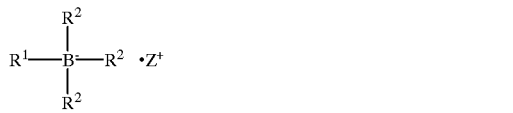

(1)

13 Claims, No Drawings

PROCESS FOR PRODUCING BORON COMPOUNDS

This application is the national phase of PCT/JP98/00477, filed Feb. 5, 1998, now WO98/34938.

TECHNICAL FIELD

The present invention relates to a method of producing a boron-based compound and more particularly to a method of producing a boron-based compound useful as a photopolymerization initiator or a light-absorbing decolorizing agent.

BACKGROUND ART

Photopolymerization is used in a variety of applications such as hardening of coated films, lithography, resin relief, and preparation of printed board, resist or photomask, black and white or color transfer development or preparation of color developing sheet. Also, in the area of dental technology, photopolymerizable compositions are used.

Photopolymerizable compositions comprise an ethylenically unsaturated compound and a photopolymerization initiator and usually they are polymerized by means of ultraviolet rays.

For example, there has been known a polymerizable composition that contains an α-ketocarbonyl compound as a photopolymerization initiator and hardens by irradiation of ultraviolet rays in the presence of amines such as N,N-dimethylaniline, which composition is used for producing a dental filler and a dental sealant, for producing a crown or a bridge, and for producing dental prosthesis (Japanese Patent Application Laid-open No. Sho 63-99858). Also, development of ultraviolet hardening ink has been made actively (Japanese Patent Application Laid-open No. Hei 2-22370).

However, such a photopolymerization as involving irradiation of ultraviolet rays has the problems that ultraviolet rays penetrate monomers insufficiently, ultraviolet rays generate ozone and cause irritation to the skin, and so on.

Accordingly, on photopolymerization initiators free of such problems, the applicant has previously filed a patent application relating to a composition that comprising a boron compound (sensitizer) that can initiate polymerization at high sensitivity with visible light and a (cationic) organic dye having an absorption in visible light region (Japanese Patent Application Laid-open No. Hei 5-59110) and a patent application relating to a composition comprising a boron compound that can initiate polymerization at high sensitivity with near-infrared light and a near-infrared light-absorbing cationic dye (Japanese Patent Application Laid-open No. Hei 5-194619).

Also, there has been developed a decolorizing agent that utilizes the phenomenon that the reaction between a dye and a boron-based compound with near-infrared light causes the color of the dye to disappear (Japanese Patent Application Laid-open No. Hei 4-362935) and it is applied to toners and inks that allow reuse of a recording material.

The above-mentioned photopolymerization initiator or decolorizing agent uses as the boron-based compound (sensitizer) a compound represented by general formula (A)

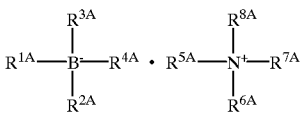

(A)

(wherein $R^{1A}$, $R^{2A}$, $R^{3A}$, and $R^{4A}$ independently represent an alkyl group, an aryl group, an alkaryl group, an allyl group, an aralkyl group, an alkenyl group, an alicyclic group or a saturated or unsaturated heterocyclic group or the like, $R^{5A}$, $R^{6A}$, $R^{7A}$, and $R^{8A}$ independently represent a hydrogen atom, an alkyl group, an aryl group, an alkaryl group, an allyl group, an aralkyl group an alkenyl group, an alicyclic group, or a saturated or unsaturated heterocyclic group or the like); of these compounds, those in which at least one of $R^{1A}$, $R^{2A}$, $R^{3A}$, and $R^{4A}$ represents an alkyl group and the remaining groups are each an aryl group are preferred.

As a general method of producing tetramethylammonium methyl triphenyl borate ($R^{1A}$=a methyl group, $R^{2A}$=$R^{3A}$=$R^{4A}$=a phenyl group, $R^{5A}$=$R^{6A}$=$R^{7A}$=$R^{8A}$=a methyl group), one of such preferred compounds, there has been known a method in which lithium methyl triphenyl borate obtained from triphenylborane and methyllithium is ion-exchanged with tetramethylammonium bromide [for example, Journal of the American Chemical Society, Vol. 107, page 6710 (1985)].

Also, as the method of producing triphenylborane, i.e., starting material, there has been generally known a method in which magnesium, boron trifluoride diethyl etherate, and phenyl bromide are reacted in diethyl ether [for example, Journal of Organic Chemistry, Vol. 51, page 427 (1986)].

In the case of the tetramethylammonium methyl triphenyl borate, concretely, its production is performed by reacting phenyl bromide with magnesium in diethyl ether to prepare a Grignard reagent, dripping it in a solution of boron trifluoride diethyl etherate in diethyl ether, and then stirring for several hours to obtain triphenylborane, followed by addition of methyllithium without isolating triphenylborane to convert it to lithium methyl triphenyl borate and by addition of tetramethylammonium bromide to effect ion exchange to obtain tetramethylammonium methyl triphenyl borate.

In such conventional production methods, diethyl ether is exclusively used as a solvent for a Grignard reaction or a triarylborane or trialkylborane reaction. This is because when use is made of tetrahydrofuran, in which the reaction is generally supposed to tend to occur more readily than in diethyl ether, the reaction does not stop when triaryl (or trialkyl) borane is produced but proceeds until tetraaryl (or tetraalkyl) borate is produced [for example, Journal of Organic Chemistry, Vol. 51, page 427 (1986)].

However, there arises the problem that a Grignard reaction is difficult to occur in diethyl ether depending on the type of halide to be used so that it takes a long time for the production and the final yield of the target boron-based compound is decreased.

OBJECT OF THE INVENTION

An object of the present invention is to obviate these problems associated with the conventional production methods and to provide a production method that enables one to obtain a highly pure boron-based compound useful as a photopolymerization initiator or light-absorbing decolorizing agent in a high yield for a short time.

DISCLOSURE OF THE INVENTION

As a result of intensive research with view to dissolving the above-mentioned problems, the present inventors have found that the above-described object can be achieved by performing reaction using a specified starting material, reaction solvent and reaction step, thereby completing the present invention.

That is, the present invention provides:

1) A method of producing a boron-based compound represented by general formula (1)

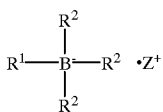
(1)

(wherein $R^1$ and $R^2$ independently represent an alkyl group which may have a substituent group, an alkenyl group which may have a substituent group, an aryl group which may have a substituent group, an aralkyl group which may have a substituent group, a heterocyclic group which may have a substituent group, or an alicyclic group which may have a substituent group provided that $R^1$ and $R^2$ are different from each other and $Z^+$ represents an ammonium cation, a pyridinium cation, a sulfonium cation, an oxosulfonium cation, a phosphonium cation, or a iodonium cation), comprising a first step of reacting lithium, magnesium or a compound containing lithium, a compound represented by general formula (2)

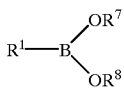
(2)

(wherein $R^1$ has the same meaning as defined above, $R^7$ and $R^8$, which may be the same or different, each represent an alkyl group which may have a substituent group, an alkenyl group which may have a substituent group, an aryl group which may have a substituent group, an aralkyl group which may have a substituent group, or an alicyclic group which may have a substituent group, or $R^7$ and $R^8$ combine with each other together with the boron atom and oxygen atoms to which they are attached to form a cyclic structure), and a compound represented by general formula (3)

$$R^2—Y \quad (3)$$

(wherein $R^2$ has the same meaning as defined above but is different from $R^1$ in the general formula (2) above and Y represents a hydrogen atom or a halogen atom) to produce a borate metal salt represented by general formula (4)

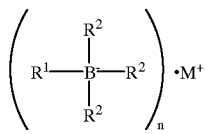
(4)

(wherein $R^1$ and $R^2$ have the same meanings as defined above, M is lithium or magnesium and n is 1 when M is lithium or 2 when M is magnesium), and a second step of adding to the borate metal salt an onium halide represented by general formula (5)

$$Z^+·X^- \quad (5)$$

(wherein $Z^+$ has the same meaning as defined above and $X^-$ represents a halide anion) to effect ion exchange reaction.

2) The method of producing a boron-based compound represented by general formula (1) as described in 1) above, wherein the onium halide represented by the general formula (5) is an ammonium halide represented by general formula (6)

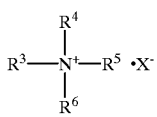
(6)

(wherein $X^-$ has the same meaning as defined above and $R^3$, $R^4$, $R^5$, and $R^6$ independently represent an alkyl group which may have a substituent group, an aryl group which may have a substituent group, an aralkyl group which may have a substituent group, or an alicyclic group which may have a substituent group).

3) The method of producing a boron-based compound represented by the general formula (1) as described in 1) or 2) above, wherein in the first step, lithium, magnesium or the compound containing lithium and the compound represented by the general formula (3) are reacted in a solvent and then the compound represented by the general formula (2) is added to obtain the borate metal salt represented by the general formula (4).

4) The method of producing a boron-based compound represented by the general formula (1) as described in 1) or 2) above, wherein in the first step, a product obtained by reacting lithium, magnesium or the compound containing lithium and the compound represented by the general formula (3) in a solvent is added to the compound represented by the general formula (2) to obtain the borate metal salt represented by the general formula (4).

5) The method of producing a boron-based compound represented by the general formula (1) as described in 1) or 2) above, wherein in the first step, lithium, magnesium or the compound containing lithium and the compound represented by the general formula (3) are reacted in a solvent in the presence of the compound represented by the general formula (2) to obtain the borate metal salt represented by the general formula (4).

6) The method of producing a boron-based compound represented by the general formula (1) as described in any of 1) to 5) above, wherein in the first step, lithium or magnesium is used and a halide is used as the compound represented by the general formula (3).

7) The method of producing a boron-based compound represented by the general formula (1) as described in any of 1) to 5) above, wherein in the first step, an organic lithium compound is used and a halide is used as the compound represented by the general formula (3).

DETAILED DESCRIPTION OF THE INVENTION $R^1$ and $R^2$ in the general formula (1) above that represents the boron-based compound produced by the method of the present invention independently represent an alkyl group which may have a substituent group, an alkenyl group which may have a substituent group, an aryl group which may have a substituent group, an aralkyl group which may have a substituent group, a heterocyclic group which may have a substituent group, or an alicyclic group which may have a substituent group. Note that $R^1$ and $R^2$ differ from each other.

$Z^+$ represents an ammonium cation, a pyridinium cation, a sulfonium cation, an oxosulfonium cation, a phosphonium cation, or a iodonium cation. Preferred $Z^+$ is an ammonium cation represented by general formula (7).

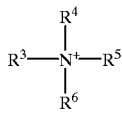

(7)

In the general formula (7), $R^3$, $R^4$, $R^5$, and $R^6$ independently represent an alkyl group which may have a substituent group, al aryl group which may have a substituent group, an aralkyl group which may have a substituent group, or an alicyclic group which may have a substituent group.

The alkyl group which may have a substituent group represented by $R^1$ and $R^2$ is preferably a substituted or unsubstituted, straight or branched chain alkyl group having 1 to 10 carbon atoms and specific examples thereof include methyl, ethyl, propyl, isopropyl, butyl, isobutyl, sec-butyl, pentyl, hexyl, heptyl, octyl, 3-methoxypropyl, 4-chlorobutyl, 2-diethylaminoethyl, etc. groups.

The alkenyl group which may have a substituent group represented by $R^1$ and $R^2$ is preferably substituted or unsubstituted and has 2 to 12 carbon atoms. Specific examples thereof include vinyl, propenyl, butenyl, pentenyl, hexenyl, heptenyl, octenyl, dodecenyl, prenyl, etc. groups.

The aryl group which may have a substituent group represented by $R^1$ and $R^2$ is a substituted or unsubstituted aryl group and specific examples thereof include phenyl, tolyl, xylyl, 4-ethylphenyl, 4-butylphenyl, 4-tert-butylphenyl, 4-methoxyphenyl, 4-diethylaminophenyl, 2-methylphenyl, 2-methoxyphenyl, naphthyl, 4-methylnaphthyl, etc. groups.

The aralkyl group which may have a substituent group represented by $R^1$ and $R^2$ is a substituted or unsubstituted aralkyl group and specific examples thereof include benzyl, phenethyl, propiophenyl, α-naphthylmethyl, β-naphthylmethyl, p-methoxybenzyl, etc. groups.

The heterocyclic group which may have a substituent group represented by $R^1$ and $R^2$ is a substituted or unsubstituted heterocyclic group and specific examples thereof include pyridyl, quinolyl, methylpyridyl, indolyl, etc. groups.

The alicyclic group which may have a substituent group represented by $R^1$ and $R^2$ is a substituted or unsubstituted alicyclic group and specific examples thereof include cyclohexyl, 4-methylcyclohexyl, cyclopentyl, cycloheptyl, etc. groups.

Specific examples of the ammonium cation of which $Z^+$ in the general formula (1) above is represented by the general formula (7) include tetramethylammonium cation, tetraethylammonium cation, tetrapropylammonium cation, tetra-n-butylammonium cation, tetra-n-pentylammonium cation, tetra-n-octylammonium cation, tetrabenzylammonium cation, tetraphenylammonium cation, tetracyclohexylammonium cation, triphenylphenacylammonium cation, triphenyl(4-aminophenyl)ammonium cation, etc.

Specific examples of the sulfonium cation represented by $Z^+$ in the general formula (1) above include dimethyl-tert-butylsulfonium cation, dimethylbenzylsulfonium cation, dimethyl(4-chlorobenzyl)sulfonium cation, dibutyl(4-bromobenzyl)sulfonium cation, dimethyl(4-cyanobenzyl)sulfonium cation, dimethylphenacylsulfonium cation, tributylsulfonium cation, triphenylsulfonium cation, etc.

Specific examples of the pyridinium cation represented by $Z^+$ in the general formula (1) above include N-methylpyridinium cation, N-ethylpyridinium cation, N-n-propylpyridinium cation, N-n-butylpyridinium cation, etc.

Specific examples of the oxosulfonium cation represented by $Z^+$ in the general formula (1) above include dimethyl-tert-butyloxosulfonium cation, dimethylbenzyloxosulfonium cation, dimethyl(4-chlorobenzyl)oxosulfonium cation, dibutyl(4-bromobenzyl)oxosulfonium cation, dimethyl(4-cyanobenzyl)oxosulfonium cation, dimethylphenacyloxosulfonium cation, tributyloxosulfonium cation, triphenyloxosulfonium cation, etc.

Specific examples of the phosphonium cation represented by $Z^+$ in the general formula (1) above include tetramethylphosphonium cation, tetraethylphosphonium cation, tetrapropylphosphonium cation, tetra-n-butylphosphonium cation, tetra-n-pentylphosphonium cation, tetra-n-octylphosphonium cation, tetrabenzylphosphonium cation, tetraphenylphosphonium cation, tetracyclohexylphosphonium cation, triphenylphenacylphosphonium cation, triphenyl(4-aminophenyl)phosphonium cation, etc.

Specific examples of the iodonium cation represented by $Z^+$ in the general formula (1) above include diphenyliodonium cation, 4-butoxyphenyl(4'-methylphenyl)iodonium cation, bis(4-aminophenyl)iodonium cation, etc.

Specific examples of the boron-based compounds represented by the general formula (1) include tetramethylammonium ethyl tri-n-butyl borate,
tetra-n-butylammonium phenethyl trimethyl borate,
tetraethylammonium phenyl truisobutyl borate,
tetra-n-butylammonium phenethyl tri(4-methylphenyl) borate,
tetramethylammonium ethyl triphenyl borate,
tetraethylammonium n-octyl tri(4,5-diethylphenyl)borate,
tetra-n-butylammonium n-pentyl tri(4-methoxyphenyl) borate,
tetra-n-octylammonium n-butyl tri-1-naphthyl borate,
tetra-n-butylammonium n-butyl tri(4-methyl-1-naphthyl) borate,
tetraethylammonium n-octyl tri(4,5-diethyl-1-naphthyl) borate,
tetra-n-butylammonium ethyl triacenaphthyl borate,
N-methylpyridinium n-butyl triphenyl borate,
triphenylsulfonium n-butyl tri(1-naphthyl)borate,
triphenyloxosulfonium n-butyl tri(1-naphthyl)borate,
tetra-n-butylsulfonium n-butyl triphenyl borate,
diphenyliodonium n-butyl triphenyl borate, etc.

$R^1$ in the general formula (2) above is the same as $R^1$ in the general formula (1) above. $R^7$ and $R^8$ in the general formula (2) above, which may be the same or different, $R^7$ and $R^8$, which may be the same or different, each represent an alkyl group which may have a substituent group, an alkenyl group which may have a substituent group, an aryl group which may have a substituent group, an aralkyl group which may have a substituent group, or an alicyclic group which may have a substituent group, or $R^7$ and $R^8$ combine with each other together with the boron atom and oxygen atoms to which they are attached to form a cyclic structure.

The alkyl group which may have a substituent group represented by $R^7$ and $R^8$ is preferably a substituted or unsubstituted, straight or branched chain alkyl group having 1 to 10 carbon atoms and specific examples thereof include methyl, ethyl, propyl, isopropyl, butyl, isobutyl, sec-butyl, pentyl, hexyl, heptyl, octyl, 3-methoxypropyl, 4-chlorobutyl, 2-diethylaminoethyl, etc. groups.

The alkenyl group which may have a substituent group represented by $R^7$ and $R^8$ is a substituted or unsubstituted alkenyl group and has preferably 2 to 12 carbon atoms. Specific examples thereof include vinyl, propenyl, butenyl, pentenyl, hexenyl, heptenyl, octenyl, dodecenyl, prenyl, etc. groups.

The aryl group which may have a substituent group represented by $R^7$ and $R^8$ is a substituted or unsubstituted aryl group and specific examples thereof include phenyl, tolyl, xylyl, 4-ethylphenyl, 4-butylphenyl, 4-tert-butylphenyl, 4-methoxyphenyl, 4-diethylaminophenyl, 2-methylphenyl, 2-methoxyphenyl, naphthyl, 4-methylnaphthyl, etc. groups.

The aralkyl group which may have a substituent group represented by $R^7$ and $R^8$ is a substituted or unsubstituted aralkyl group and specific examples thereof include benzyl, phenethyl, propiophenyl, α-naphthylmethyl, β-naphthylmethyl, p-methoxybenzyl, etc. groups.

The alicyclic group which may have a substituent group represented by $R^7$ and $R^8$ is a substituted or unsubstituted alicyclic group and specific examples thereof include cyclohexyl, 4-methylcyclohexyl, cyclopentyl, cycloheptyl, etc. groups.

Specific examples of the compound represented by the general formula (2) above include dimethyl ethyl boronate, diethyl n-propyl boronate, diisopropyl n-butyl boronate, diisobutyl methyl boronate, di-n-octyl benzyl boronate, di(2-phenethyl)n-butyl boronate, diphenyl n-propyl boronate, diisopropyl phenyl boronate, diethyl(4-methoxyphenyl)boronate, dicyclohexyl n-octyl boronate, etc.

Specific examples of the compound having a cyclic structure represented by $R^7$ and $R^8$ together with the boron atom and oxygen atoms to which they are attached include 2-methyl-1,3,2-dioxaborinane, 2-ethyl-1,3,2-dioxaborinane, 2-n-propyl-1,3,2-dioxaborinane, 2-n-butyl-1,3,2-dioxaborinane, 2-phenyl-1,3,2-dioxaborinane, 2-naphthyl-1,3,2-dioxaborinane, etc.

$R^2$ in the general formula (3) above is the same as $R^2$ in the general formula (1) above and Y represents a hydrogen atom or a halogen atom.

The compound represented by the general formula (3) above includes halides of saturated or unsaturated aliphatic hydrocarbons, halides of alicyclic hydrocarbons, halides of aromatic hydrocarbons, aromatic hydrocarbons, heterocyclic aromatic compounds, etc. Specific examples thereof include methyl bromide, ethyl chloride, propyl chloride, isopropyl chloride, butyl chloride, isobutyl bromide, pentyl bromide, hexyl bromide, octyl chloride, 2-bromoethyl methyl ether, vinyl bromide, propenyl bromide, butenyl bromide, pentenyl bromide, hexenyl bromide, heptenyl bromide, octenyl bromide, bromobenzene, iodobenzene, bromotoluene, bromoxylene, 1-bromo-4-ethylbenzene, 1-bromo-4-butylbenzene, 1-bromo-4-tert-butylbenzene, 1-bromo-4-methoxybenzene, 1-bromo-4-diethylaminobenzene, 1-bromo-2-methylbenzene, 1-bromo-2-methoxybenzene, 1-bromonaphthalene, 2-bromonaphthalene, 1-bromo-4-methylnaphthalene, benzyl chloride, phenethyl bromide, 1-bromo-3-phenylpropane, 1-(bromomethyl)naphthalene, 2-(bromomethyl)naphthalene, p-methoxybenzyl chloride, cyclohexyl chloride, 1-chloro-4-methylcyclohexane, benzene, toluene, xylene, ethylbenzene, butylbenzene, tert-butylbenzene, methoxybenzene, diethylaminobenzene, ethoxybenzene, naphthalene, 1-methylnaphthalene, cyclopentadiene, indene, fluorene, furan, thiophene, etc.

Specific examples of the onium halide represented by the general formula (5) include tetramethylammonium bromide, tetraethylammonium bromide, tetra-n-propylammonium iodide, tetra-n-butylammonium bromide, tetra-n-pentylammonium chloride, tetra-n-octylammonium bromide, tetrabenzylammonium bromide, tetraphenylammonium bromide, tetracyclohexylammonium bromide, N-methylpyridinium chloride, N-butylpyridinium bromide, dimethyl-tert-butylsulfonium bromide, dimethylbenzylsulfonium bromide, dimethyl(4-chlorobenzyl)sulfonium bromide, dibutyl(4-bromobenzyl)sulfonium chloride, dimethyl(4-cyanobenzyl)sulfonium bromide, dimethylphenacylsulfonium chloride, tributylsulfonium chloride, triphenylsulfonium chloride, tributylsulfonium bromide, triphenylsulfonium bromide, dimethyl-tert-butyloxosulfonium bromide, dimethylbenzyloxosulfonium bromide, dimethyl(4-chlorobenzyl)oxosulfonium chloride, dibutyl(4-dimethyl(4-cyanobenzyl)oxosulfonium chloride, dimethylphenacyloxosulfonium chloride, tributyloxosulfonium chloride, triphenyloxosulfonium chloride, tributyloxosulfonium bromide, triphenyloxosulfonium bromide, tetramethylphosphonium chloride, tetraethylphosphonium chloride, tetra-n-propylphosphonium chloride, tetra-n-butylphosphonium bromide, tetra-n-pentylphosphonium bromide, tetra-n-octylphosphonium chloride, tetrabenzylphosphonium chloride, tetraphenylphosphonium iodide, tetracyclohexylphosphonium bromide, tetraphenylphosphonium bromide, triphenylphenacylphosphonium chloride, triphenyl(4-aminophenyl)phosphonium bromide, diphenyliodonium chloride, 4-butoxyphenyl(4'-methylphenyl)iodonium chloride, bis(4-aminophenyl)iodonium chloride, etc.

$R^1$ and $R^2$ in the general formula (4) representing the borate metal salt have the same meanings as defined above. M represents a lithium or magnesium atom and n is 1 when M is lithium or 2 when M is magnesium.

In the present invention, the compound containing lithium used in the first step is an organic lithium compound such as an alkyllithium or an aryllithium. Specific examples thereof include methyllithium, n-butyllithium, phenyllithium, etc. Of these, preferred is n-butyllithium.

The solvent used in the present invention includes, for example, ether-based solvents such as diethyl ether, n-butyl ethyl ether, di-n-propyl ether, diisopropyl ether, di-n-butyl ether, 1,2-dimethoxyethane, tetrahydrofuran, and 1,4-dioxane, hydrocarbon-based solvents such as n-hexane, aromatic-based solvents such as benzene, toluene, and xylene. Of these, diethyl ether, tetrahydrofuran, hexane, and toluene are used preferably.

According to the method of the present invention, first, in the first step, lithium, magnesium or the compound containing lithium and the compound represented by the general formula (2), and the compound represented by the general formula (3) are reacted to produce the borate metal salt represented by the general formula (4), an intermediate.

More specifically, the first step is carried out, for example, by the following methods:

(a) A method in which lithium, magnesium or the compound containing lithium and the compound represented by the general formula (3) are reacted in a solvent and thereafter the compound represented by the general formula (2) is added thereto for reaction to obtain the compound represented by the general formula (4), (b) A method in which to the compound represented by the general formula (2) is added a product obtained by reacting lithium, magnesium or the compound containing lithium and the compound represented by the general formula (3) in a solvent to obtain the compound represented by the general formula (4), and (c) A method in which lithium, magnesium or the compound containing lithium and the compound represented by the general formula (3) are reacted in a solvent in the presence of the compound represented by the general formula (2) to obtain the borate metal salt represented by the general formula (4).

Next, in the second step, to the previously obtained borate metal salt intermediate represented by the general formula (4) is added the onium halide represented by the general formula (5) to effect ion exchange reaction to produce the boron-based compound represented by the general formula (1).

More specifically, for example, use of magnesium and a halide as the compound represented by the general formula (3) and reaction by any of the methods (a), (b) or (c) above in the first step enables production of a borate magnesium salt intermediate represented by the general formula (4) in which M is Mg and n is 2.

Also, use of lithium and a halide as the compound represented by the general formula (3) and reaction by the method (a) or (b) in the first step enables production of a borate lithium salt intermediate represented by the general formula (4) in which M is Li and n is 1.

Also, use of an organic lithium compound and a halide as the compound represented by the general formula (3) and reaction by the method (a) or (b) in the first step also enables a borate lithium salt intermediate represented by the general formula (4) in which M is Li and n is 1.

Use of a halide as the compound represented by the general formula (3) generally increases yield.

An example of reaction for producing a borate magnesium salt intermediate represented by the general formula (4) in which M is Mg and n is 2 using magnesium will be described concretely.

In this case, the reaction between (a), (b) and (c) is a reaction for preparing a Grignard reagent. Accordingly, the compound represented by the general formula (3) must be a halide.

Addition of a small amount of an ether solution of a halide to magnesium and stirring results in an elevation in reaction temperature before long and reaction (Grignard reaction) starts. If the reaction is difficult to occur, iodine, methyl iodide, etc. may be added as an initiator. The reaction temperature is preferably near the boiling point of the solvent to be used and an ether-based solution of the halide is added so that this temperature can be maintained.

For example, in tetrahydrofuran, it is desirable to add a tetrahydrofuran solution of halide so that the reaction proceeds at a temperature near 67 to 72° C. After the addition of the ether solution of halide the resulting mixture is stirred at a temperature from room temperature to near the boiling point of the solvent for about 30 minutes to about 20 hours to complete the reaction. The compound thus prepared is a Grignard reagent.

In the case of the reaction (a) above, a solution of the compound represented by the general formula (2) (preferably a solution using the same solvent as the solvent used for the Grignard reaction) is added to the Grignard reagent such that the reaction temperature will be from room temperature to near the boiling point of the solvent used and after the addition, the mixture is allowed to react at from room temperature to near the boiling point of the solvent for about 30 minutes to about 2 hours, thereby completing the first step.

In the case of the reaction (b) above, to a solution of the compound represented by the general formula (2) (preferably the same solvent as the solvent used for the Grignard reaction) is added the Grignard reagent such that the reaction temperature will be at from room temperature to near the boiling point of the solvent used and after the addition, the mixture is allowed to react at from room temperature to near the boiling point of the solvent for about 30 minutes to about 2 hours, thereby completing the first step.

In the case of the reaction (c) above, addition of a small amount of an ether solution of a halide to magnesium and the compound represented by the general formula (2) and stirring results in an elevation in reaction temperature before long and reaction (Grignard reaction) starts. If the reaction is difficult to occur, iodine, methyl iodide, etc. may be added as an initiator. The reaction temperature is preferably near the boiling point of the solvent to be used and an ether-based solution of the halide is added so that this temperature can be maintained. For example, in tetrahydrofuran, it is desirable to add a tetrahydrofuran solution of a halide so that the reaction proceeds at a temperature near 67 to 72° C. After the addition of the ether solution of a halide the resulting mixture is stirred at a temperature from room temperature to near the boiling point of the solvent for about 30 minutes to about 20 hours to complete the first step.

As described above, when a Grignard reaction using magnesium is to be passed through, the compound represented by the general formula (3) must be a halide.

In the conventional method, the solvent for Grignard reactions is limited to diethyl ether as described above. On the contrary, in the present invention, it is possible to use as a solvent tetrahydrofuran or the like, in which Grignard reactions tend to occur more readily, so that the reaction time is shortened and yield increases.

When lithium or an organic lithium compound is used instead of magnesium, the compound represented by the general formula (3) does not have to be a halide. However, when the compound represented by the general formula (3) is a halide, substitution of a halogen by lithium proceeds selectively as described later on.

When the compound represented by the general formula (3) is not a halide, it is considered that there are a plurality of organic lithium compounds that have been lithiated with lithium or an organic lithium compound (for example, in the case of lithiation of trifluoromethylbenzene, there are at least three kinds of lithium compounds) and hence yield is increased when the compound represented by the general formula (3) is a halide.

An example of reaction for producing an intermediate compound represented by the general formula (4) in which M is Li and n is 1 using lithium will be described concretely.

This intermediate compound can be produced by use of lithium and a halide as the compound represented by the general formula (3) and by means of the method (a) or (b) above in the first step. In this case, as the solvent there can be used ether-based solvents such as diethyl ether and solvents such as tetrahydrofuran and solvents such as hexane and cyclohexane. In this case, generally the reaction is carried out in the presence of an inert gas at from about −100° C. to about room temperature.

More specifically, such a solvent as described above is added to lithium and a halide solution is added thereto. The reaction temperature may vary depending on the halide and solvent used. For example, in the reaction between lithium and dibromobenzene in diethyl ether, it is desirable to add a diethyl ether solution of bromobenzene such that the reaction temperature will be from −78 to −70° C. After addition of the halide solution, the resulting mixture is stirred at from about −100° C. to about room temperature for about 30 minutes to about 2 hours to prepare an organic lithium compound.

And in the case of the reaction (a) above, a solution of the compound represented by the general formula (2) in such a solvent as described above (preferably, an ether-based solution) is added to the organic lithium compound such that the reaction temperature will be preferably about −100° C. to about room temperature and after the addition, the mixture is allowed to react at from about −100° C. to about room temperature for about 30 minutes to about 2 hours to complete the first step.

In the case of the reaction (b) above, an organic lithium compound is added to a solution of the compound represented by the general formula (2) in such a solvent as described above (preferably, an ether-based solvent) such that the reaction temperature will be preferably from about −100° C. to about room temperature and after the addition, the mixture is allowed to react at from about −100° C. to about room temperature for about 30 minutes to about 2 hours to complete the first step.

Next, an example of reaction for producing an intermediate represented by the general formula (4) in which M is Li and n is 1 using an organic lithium compound will be described concretely.

This intermediate compound can also be produced by use of an organic lithium compound and an aromatic halide as the compound represented by the general formula (3) as described above and by means of the method (a) or (b) above in the first step.

Some of the organic lithium compounds are put on the market in the form of a hexane solution, a cyclohexane solution, a diethyl ether solution, etc. and readily available.

When organic lithium compounds are used, the reaction solvent which can be used includes ether-based solvents such as diethyl ether and tetrahydrofuran, solvents such as cyclohexane, etc.

Generally, the reaction proceeds in an inert gas atmosphere at from about −100° C. to about room temperature. A solution of halide is added to a solution of organic lithium compound such that the reaction temperature will be from about −100° C. to about room temperature to prepare an organic lithium compound. The reaction temperature may vary depending on the halide and solvent to be used. For example, the reaction of n-butyllithium and 1-bromo-2,5-dimethylbenzene in diethyl ether is desirably performed by addition of a diethyl ether solution of 1-bromo-2,5-dimethylbenzene such that the reaction occurs at from −78 to −10° C. After the addition is completed, the resulting mixture is further stirred at from about −100° C. to about room temperature for about 30 minutes to about 2 hours to prepare an organic lithium compound. Also, an organic compound can be prepared by adding a solution of organic lithium compound to a solution of halide under similar conditions.

In the case of the reaction (a), a solution of the compound represented by the general formula (2) in such a solvent as described above (preferably, an ether-based solution) is added to the organic lithium compound such that the reaction temperature will be preferably from about −100° C. to about room temperature and after the addition, the mixture is allowed to react at from about −100° C. to about room temperature for about 30 minutes to about 2 hours to complete the first step.

In the case of the reaction (b) above, an organic lithium compound is added to a solution of the compound represented by the general formula (2) in such a solvent as described above (preferably, an ether-based solvent) such that the reaction temperature will be preferably from about −100° C. to about room temperature and after the addition, the mixture is allowed to react at from about −100° C. to about room temperature for about 30 minutes to about 2 hours to complete the first step.

More specifically, the second step in the present invention can proceed, for example, as follows.

The intermediate compound (borate metal salt) represented by the general formula (4) after the completion of the first step is distributed in water and a suitable organic solvent (preferably, ethyl acetate or diethyl ether) and 1.2 to 5 equivalents of the onium halide represented by the general formula (5) is added to the aqueous phase, followed by vigorous stirring to cause ion exchange of the metal cation portion of borate with the onium cation. Further, the reaction mixture is washed with water once or twice and only the organic layer is distilled off under reduced pressure. To the residue is added a solvent such as diethyl ether, hexane or methanol and the precipitates are filtered and washed with a solvent such as diethyl ether or hexane.

According to the conventional production method, for example, in the case the compound represented by the general formula (1) is tetra-n-butylammonium n-butyl tri(4-methylphenyl)borate, it is sometimes the case that tetra(4-methylphenyl)borate is by-produced as a result of a side reaction upon production of tri(4-methylphenyl)borane so that yield is decreased. On the contrary, according to the method of the present invention, there is no possibility that the side reaction will occur so that a high purity boron-based compound can be obtained.

Use of the production method of the present invention not only increases yield but also shortens production time as compared with the conventional method.

For example, in the case of the above-mentioned tetra-n-butylammonium n-butyl tri(4-methylphenyl)borate, the conventional method is carried out by (i) adding to magnesium a diethyl ether solution of 4-bromotoluene to prepare a Grignard reagent, (ii) reacting the Grignard reagent with boron trifluoride diethyl etherate in diethyl ether to derive it to a triarylborane, (iii) further reacting the triarylborane with an organic metal compound selected from n-butylmagnesium chloride, n-butylmagnesium bromide, n-butylmagnesium iodide and n-butyllithium to derive it to n-butyl tri(4-methylphenyl)borate metal salt, and then (iv) subjecting the borate metal salt to ion exchange with tetra-n-butylammonium bromide to obtain the target compound (tetra-n-butylammonium n-butyl tri(4-methylphenyl) borate). Therefore, the conventional method comprises 4 steps and it takes about 10 hours for the production in this case.

On the other hand, in the case of the production method of the present invention, in particular, in the case where a halide is used as the compound represented by the general formula (3) and magnesium and the halide represented by the general formula (3) are reacted in the presence of the compound represented by the general formula (2) in tetrahydrofuran, a tetrahydrofuran solution of 4-bromotoluene is added to magnesium and diisopropyl n-butyl boronate to cause Grignard reaction and derive the boronate to n-butyl tri(4-methylphenyl)borate metal salt (the first step). Then, theboratemetal salt is subjected to ion exchange with tetra-n-butylammonium bromide, which enables one to obtain tetra-n-butylammonium n-butyl tri(4-methylphenyl)borate, the target compound (the second step). Therefore, the target compound can be produced in 2 steps so that production in a short time of about 4 hours, for example, is possible.

BEST MODE FOR CARRYING OUT THE INVENTION

Hereafter, the present invention will be described in more detail by example. However, the present invention should not be limited to the following examples without departing from the gist of the present invention.

EXAMPLE 1

Production of tetra-n-butylammonium methyl tri(4-methylphenyl)borate

First Step

To 1.00 g (41.1 mmol) of magnesium were added 10 mg of iodine and 10 ml of tetrahydrofuran. To this was added dropwise a solution of 5.64 g (33.0 mmol) of 4-bromotoluene in 20 ml of tetrahydrofuran in a nitrogen atmosphere such that the reaction temperature was from 67 to 72° C. and the mixture was further stirred at from 30 to 50° C. for 2 hours. To this was added 1.00 g (10.0 mmol) of 2-methyl-1,3,2-dioxaborinane at the same temperature as above and the resulting mixture was further stirred at from 30 to 50° C. for 2 hours.

Second Step

When the reaction mixture was cooled to room temperature, 200 ml of diethyl ether was added and then 50 ml of water was added portionwise. The reaction mixture was transferred into a separatory funnel and washed with 80 ml of water, 60 ml of an aqueous 0.2 M tetra-n-butylammonium bromide solution, and 80 ml of water in order, and then concentrated. To the residue was added 200 ml of diethyl ether and the solids which precipitated were filtered to obtain 5.00 g (9.23 mmol) of the target compound as white solids in a yield of 92%.

Measurement of mass spectrum of the product gave a value of 299 for the anion portion and 242 for the cation portion, thus showing coincidence with the calculated values. Also, elemental analysis indicated coincidence with the calculated values.

Elemental Analysis:

| Calculated (%) | C 84.26 | H 11.26 | N 2.59 | B 2.00 |
|---|---|---|---|---|
| Found (%) | C 84.11 | H 11.31 | N 2.44 | B 2.14 |

EXAMPLE 2

Production of tetramethylammonium n-butyl tri-n-octyl borate

First Step

To 1.00 g (41.1 mmol) of magnesium was added dropwise a solution of 4.91 g (33.0 mmol) 1-chlorooctane in 20 ml of diethyl ether in a nitrogen atmosphere to prepare a Grignard reagent.

The Grignard reagent was added dropwise in a solution of 1.86 g (10.0 mmol) of diisopropyl n-butyl boronate in 10 ml of tetrahydrofuran such that the reaction temperature did not exceed 50° C. Further, the mixture was stirred at from 30 to 50° C. for 2 hours to complete the reaction.

Second Step

When the reaction mixture was cooled to room temperature, 200 ml of diethyl ether was added and then 50 ml of water was added portionwise. The reaction mixture was transferred into a separatory funnel and washed with 80 ml of water, 60 ml of an aqueous 0.2 M tetramethylammonium bromide solution, and 80 ml of water in order, and then concentrated. To the residue was added 200 ml of diethyl ether and the solids which precipitated were filtered to obtain 4.39 g (9.11 mmol) of the target compound as white solids in a yield of 91%.

Measurement of mass spectrum of the product gave a value of 407 for the anion portion and 74 for the cation portion, thus showing coincidence with the calculated values. Also, elemental analysis indicated coincidence with the calculated values.

Elemental Analysis:

| Calculated (%) | C 79.78 | H 15.06 | N 2.91 | B 2.24 |
|---|---|---|---|---|
| Found (%) | C 79.99 | H 15.11 | N 2.79 | B 2.11 |

EXAMPLE 3

Production of tetra-n-octylammonium benzyl triphenyl borate

First Step

To 1.00 g (41.1 mmol) of magnesium was added 10 mg of iodine. To this was added dropwise a solution of 5.18 g (33.0 mmol) of bromobenzene in 20 ml of tetrahydrofuran in a nitrogen atmosphere to prepare a Grignard reagent.

The Grignard reagent was added dropwise in a solution of 2.20 g (10.0 mmol) of diisopropyl benzyl boronate in 10 ml of tetrahydrofuran such that the reaction temperature did not exceed 50° C. Further, the mixture was stirred at from 30 to 50° C. for 2 hours to complete the reaction.

Second Step

When the reaction mixture was cooled to room temperature, 200 ml of diethyl ether was added and then 50 ml of water was added portionwise. The reaction mixture was transferred into a separatory funnel, to which were added 80 ml of water and 5.5 g (11.8 mmol) of tetra-n-octylammonium bromide, and washed with 80 ml of water, and then concentrated. To the residue was added 200 ml of diethyl ether and the solids which precipitated were filtered to obtain 7.45 g (9.31 mmol) of the target compound as white solids in a yield of 93%.

Measurement of mass spectrum of the product gave a value of 333 for the anion portion and 466 for the cation portion, thus showing coincidence with the calculated values. Also, elemental analysis indicated coincidence with the calculated values.

Elemental Analysis:

| Calculated (%) | C 85.56 | H 11.34 | N 1.75 | B 1.35 |
|---|---|---|---|---|
| Found (%) | C 85.48 | H 11.31 | N 1.99 | B 1.22 |

EXAMPLE 4

Production of tetra-n-butylammonium n-butyl tri(4-tert-butylphenyl)borate

First Step

To 1.00 g (41.1 mmol) of magnesium were added 10 mg of iodine, 1.42 g (10.0 mmol) of 2-n-butyl-1,3,2-dioxaborinane, and 10 ml of tetrahydrofuran. To this was dripped a solution of 7.03 g (33.0 mmol) of 1-bromo-4-tert-butylbenzene in 20 ml of tetrahydrofuran in a nitrogen atmosphere such that the reaction temperature was from 67 to 72° C. and further the mixture was stirred at from 30 to 50° C. for 2 hours to complete the reaction.

Second Step

When the reaction mixture was cooled to room temperature, 200 ml of diethyl ether was added and then 50 ml of water was added portionwise. The reaction mixture was transferred into a separatory funnel and washed with 80 ml of water, 60 ml of an aqueous 0.2 M tetra-n-butylammonium bromide solution, and 80 ml of water in order, and then concentrated. To the residue was added 200 ml of diethyl ether and the solids which precipitated were filtered to obtain 6.80 g (9.57 mmol) of the target compound as white solids in a yield of 95%.

Measurement of mass spectrum of the product gave a value of 467 for the anion portion and 242 for the cation portion, thus showing coincidence with the calculated values. Also, elemental analysis indicated coincidence with the calculated values.

Elemental Analysis:

| Calculated (%) | C 84.58 | H 11.92 | N 1.97 | B 1.52 |
| Found (%) | C 84.66 | H 11.91 | N 2.00 | B 1.43 |

EXAMPLE 5

Production of tetra-n-butylammonium n-butyl tri(4-methylnaphthyl)borate

First Step

To 1.00 g (41.1 mmol) of magnesium were added 10 mg of iodine, 1.86 g (10.0 mmol) of diisopropyl n-butyl boronate, and 10 ml of tetrahydrofuran. To this was added dropwise a solution of 7.30 g (33.0 mmol) of 1-bromo-4-methylnaphthalene in 20 ml of tetrahydrofuran in a nitrogen atmosphere such that the reaction temperature was from 67 to 72° C. and further the mixture was stirred at from 30 to 50° C. for 2 hours to complete the reaction.

Second Step

When the reaction mixture was cooled to room temperature, 200 ml of diethyl ether was added and then 50 ml of water was added portionwise. The reaction mixture was transferred into a separatory funnel and washed with 80 ml of water, 60 ml of an aqueous 0.2 M tetra-n-butylammonium bromide solution, and 80 ml of water in order, and then concentrated. To the residue was added 200 ml of diethyl ether and the solids which precipitated were filtered to obtain 6.75 g (9.19 mmol) of the target compound as white solids in a yield of 91%.

Measurement of mass spectrum of the product gave a value of 491 for the anion portion and 242 for the cation portion, thus showing coincidence with the calculated values. Also, elemental analysis indicated coincidence with the calculated values.

Elemental Analysis:

| Calculated (%) | C 86.73 | H 9.89 | N 2.62 | B 1.47 |
| Found (%) | C 86.91 | H 9.63 | N 2.44 | B 1.19 |

EXAMPLE 6

Production of tetraethylammonium phenyl tri(2,5-dimethylphenyl)borate

First Step

To 0.3 g (43.2 mmol) of lithium was added 10 ml of diethyl ether. To this was added dropwise a solution of 6.11 g (33.0 mmol) of 1-bromo-2,5-dimethylbenzene in 20 ml of diethyl ether in a nitrogen atmosphere such that the reaction temperature was from −75 to −65° C. and further the mixture was stirred at the same temperature as above for 2 hours. This was added dropwise in a solution of 1.62 g (10.0 mmol) of 2-phenyl-1,3,2-dioxaborinane in 10 ml of tetrahydrofuran such that the reaction temperature did not exceed 5° C. Further, the mixture was stirred at from 0 to 5° C. for 2 hours to complete the reaction.

Second Step

When the reaction mixture was elevated to room temperature, 200 ml of diethyl ether was added and then 50 ml of water was added portionwise. The reaction mixture was transferred into a separatory funnel and washed with 80 ml of water, 60 ml of an aqueous 0.2 M tetraethylammonium bromide solution, and 80 ml of water in order, and then concentrated. To the residue was added 200 ml of diethyl ether and the solids which precipitated were filtered to obtain 3.80 g (7.10 mmol) of the target compound as white solids in a yield of 71%.

Measurement of mass spectrum of the product gave a value of 403 for the anion portion and 130 for the cation portion, thus showing coincidence with the calculated values. Also, elemental analysis indicated coincidence with the calculated values.

Elemental Analysis:

| Calculated (%) | C 85.53 | H 9.82 | N 2.62 | B 2.03 |
| Found (%) | C 85.78 | H 10.01 | N 2.49 | B 1.80 |

EXAMPLE 7

Production of tetraethylammonium cyclohexyl triphenyl borate

First Step

To 0.46 g (66.0 mmol) of lithium was added 10 ml of diethyl ether. To this was added dropwise a solution of 5.18 g (33.0 mmol) of bromobenzene in 20 ml of diethyl ether in a nitrogen atmosphere such that the reaction temperature was from −75 to −65° C. and further the mixture was stirred at the same temperature as above for 2 hours. To this was added dropwise a solution of 1.62 g (10.0 mmol) of 2-cyclohexyl-1,3,2-dioxaborinane in 10 ml of tetrahydrofuran such that the reaction temperature was from 0 to 5° C. Further, the mixture was stirred at from 0 to 5° C. for 2 hours to complete the reaction.

Second Step

When the reaction mixture was elevated to room temperature, 200 ml of diethyl ether was added and then 50 ml of water was added portionwise. The reaction mixture was transferred into a separatory funnel and washed with 80 ml of water, 60 ml of an aqueous 0.2 M tetraethylammonium bromide solution, and 80 ml of water in order, and then concentrated. To the residue was added 200 ml of diethyl ether and the solids which precipitated were filtered to obtain 4.21 g (9.00 mmol) of the target compound as white solids in a yield of 90%.

Measurement of mass spectrum of the product gave a value of 333 for the anion portion and 130 for the cation portion, thus showing coincidence with the calculated values. Also, elemental analysis indicated coincidence with the calculated values.

Elemental Analysis:

| Calculated (%) | C 84.37 | H 10.81 | N 3.07 | B 2.37 |
|---|---|---|---|---|
| Found (%) | C 84.19 | H 11.00 | N 2.89 | B 2.15 |

EXAMPLE 8

Production of tetramethylammonium n-butyl trinaphthyl borate

First Step

To a solution of 6.83 g (33.0 mmol) of 1-bromonaphthalene in 20 ml of tetrahydrofuran was added 21 ml (33.6 mmol) of 1.6 M n-butyllithium under ice cooling in a nitrogen atmosphere and the mixture was stirred for 2 hours at the same temperature as above. This was added dropwise in a solution of 1.58 g (10.0 mmol) of diisopropyl ethyl boronate in 10 ml of tetrahydrofuran such that the temperature did not exceed 10° C. Further, the mixture was stirred at from 0 to 5° C. for 2 hours to complete the reaction.

Second Step

When the reaction mixture was elevated to room temperature, 200 ml of diethyl ether was added and then 50 ml of water was added portionwise. The reaction mixture was transferred into a separatory funnel and washed with 80 ml of water, 60 ml of an aqueous 0.2 M tetramethylammonium bromide solution, and 80 ml of water in order, and then concentrated. To the residue was added 200 ml of diethyl ether and the solids which precipitated were filtered to obtain 4.35 g (8.78 mmol) of the target compound as white solids in a yield of 87%.

Measurement of mass spectrum of the product gave a value of 421 for the anion portion and 74 for the cation portion, thus showing coincidence with the calculated values. Also, elemental analysis indicated coincidence with the calculated values.

Elemental Analysis:

| Calculated (%) | C 87.37 | H 7.73 | N 2.83 | B 2.18 |
|---|---|---|---|---|
| Found (%) | C 87.51 | H 7.80 | N 2.59 | B 2.23 |

EXAMPLE 9

Production of tetra-n-butylammonium butyl tri(6-methoxy-2-naphthyl)borate

First Step

To 1.00 g (41.1 mmol) of magnesium were added 10 mg of iodine, 1.86 g (10.0 mmol) of diisopropyl n-butyl boronate, and 10 ml of tetrahydrofuran. To this was added dropwise a solution of 7.82 g (33.0 mmol) of 2-bromo-6-methoxynaphthalene in 30 ml of tetrahydrofuran in a nitrogen atmosphere such that the reaction temperature was from 67 to 72° C. and further the mixture was stirred at from 30 to 50° C. for 2 hours to complete the reaction.

Second Step

When the reaction mixture was cooled to room temperature, 200 ml of diethyl ether was added and then 50 ml of water was added portionwise. The reaction mixture was transferred into a separatory funnel and washed with 80 ml of water, 60 ml of an aqueous 0.2 M tetra-n-butylammonium bromide solution, and 80 ml of water in order, and then concentrated. To the residue was added 200 ml of diethyl ether and the solids which precipitated were filtered to obtain 7.11 g (9.10 mmol) of the target compound as white solids in a yield of 91%.

Measurement of mass spectrum of the product gave a value of 540 for the anion portion and 242 for the cation portion, thus showing coincidence with the calculated values. Also, elemental analysis indicated coincidence with the calculated values.

Elemental Analysis:

| Calculated (%) | C 81.41 | H 9.28 | N 1.79 | B 1.38 |
|---|---|---|---|---|
| Found (%) | C 81.55 | H 9.46 | N 1.76 | B 1.38 |

EXAMPLE 10

Production of tetra-n-butylphosphonium butyl trinaphthyl borate

First Step

To 1.00 g (41.1 mmol) of magnesium were added 10 mg of iodine, 1.86 g (10.0 mmol) of diisopropyl n-butyl boronate, and 10 ml of tetrahydrofuran. To this was added dropwise a solution of 6.83 g (33.0 mmol) of 1-bromonaphthalene in 20 ml of tetrahydrofuran in a nitrogen atmosphere such that the reaction temperature was from 67 to 72° C. and further the mixture was stirred at from 30 to 50° C. for 2 hours to complete the reaction.

Second Step

When the reaction mixture was cooled to room temperature, 200 ml of diethyl ether was added and then 50 ml of water was added portionwise. The reaction mixture was transferred into a separatory funnel and washed with 80 ml of water, 60 ml of an aqueous 0.2 M tetra-n-butylphosphonium bromide solution, and 80 ml of water in order, and then concentrated. To the residue was added 200 ml of diethyl ether and the solids which precipitated were filtered to obtain 6.17 g (8.70 mmol) of the target compound as white solids in a yield of 87%. Measurement of mass spectrum of the product gave a value of 421 for the anion portion and 259 for the cation portion, thus showing coincidence with the calculated values. Also, elemental analysis indicated coincidence with the calculated values.

Elemental Analysis:

| Calculated (%) | C 84.73 | H 9.39 | B 1.53 |
|---|---|---|---|
| Found (%) | C 84.90 | H 9.55 | B 1.77 |

EXAMPLE 11

Production of tri-n-butylsulfonium butyl trinaphthyl borate

First Step

To 1.00 g (41.1 mmol) of magnesium were added 10 mg of iodine, 1.86 g (10.0 mmol) of diisopropyl n-butyl boronate, and 10 ml of tetrahydrofuran. To this was added dropwise a solution of 6.83 g (33.0 mmol) of 1-bromonaphthalene in 20 ml of tetrahydrofuran in a nitrogen atmosphere such that the reaction temperature was from 67 to 72° C. and further the mixture was stirred at from 30 to 50° C. for 2 hours to complete the reaction.

Second Step

When the reaction mixture was cooled to room temperature, 200 ml of diethyl ether was added and then 50 ml of water was added portionwise. The reaction mixture was transferred into a separatory funnel and washed with 80 ml of water, 60 ml of an aqueous 0.2 M tri-n-butylsulfonium iodide solution, and 80 ml of water in order, and then concentrated. To the residue was added 200 ml of diethyl ether and the solids which precipitated were filtered to obtain 5.88 g (9.00 mmol) of the target compound as white solids in a yield of 90%. Measurement of mass spectrum of the product gave a value of 421 for the anion portion and 203 for the cation portion, thus showing coincidence with the calculated values. Also, elemental analysis indicated coincidence with the calculated values.

Elemental Analysis:

| Calculated (%) | C 84.63 | H 8.80 | S 4.91 | B 1.65 |
| Found (%)      | C 85.00 | H 9.01 | S 4.77 | B 1.82 |

EXAMPLE 12

Production of diphenyliodonium butyl trinaphthyl borate

First Step

To 1.00 g (41.1 mmol) of magnesium were added 10 mg of iodine, 1.86 g (10.0 mmol) of diisopropyl n-butyl boronate, and 10 ml of tetrahydrofuran. To this was added dropwise a solution of 6.83 g (33.0 mmol) of 1-bromonaphthalene in 20 ml of tetrahydrofuran in a nitrogen atmosphere such that the reaction temperature was from 67 to 72° C. and further the mixture was stirred at from 30 to 50° C. for 2 hours to complete the reaction.

Second Step

When the reaction mixture was cooled to room temperature, 200 ml of diethyl ether was added and then 50 ml of water was added portionwise. The reaction mixture was transferred into a separatory funnel and washed with 80 ml of water, 60 ml of an aqueous 0.2 M diphenyliodonium bromide solution, and 80 ml of water in order, and then concentrated. To the residue was added 200 ml of diethyl ether and the solids which precipitated were filtered to obtain 6.43 g (9.10 mmol) of the target compound as white solids in a yield of 91%. Measurement of mass spectrum of the product gave a value of 421 for the anion portion and 281 for the cation portion, thus showing coincidence with the calculated values. Also, elemental analysis indicated coincidence with the calculated values.

Elemental Analysis:

| Calculated (%) | C 74.80 | H 5.70 | B 1.53 |
| Found (%)      | C 74.78 | H 5.88 | B 1.62 |

INDUSTRIAL APPLICABILITY

According to the present invention, a high purity boron-based compound represented by the general formula (1) above useful as a photopolymerization initiator and a light-absorbing decolorizing agent can be obtained in a short time and a high yield as compared with the conventional method.

What is claimed is:

1. A method of producing a boron-based compound represented by general formula (1)

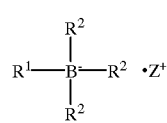

(1)

(wherein $R^1$ and $R^2$ independently represent an alkyl group which may have a substituent group, an alkenyl group which may have a substituent group, an aryl group which may have a substituent group, an aralkyl group which may have a substituent group, a heterocyclic group which may have a substituent group, or an alicyclic group which may have a substituent group provided that $R^1$ and $R^2$ are different from each other and $Z^+$ represents an ammonium cation, a pyridinium cation, a sulfonium cation, an oxosulfonium cation, a phosphonium cation, or a iodonium cation), comprising a first step of reacting lithium, magnesium or a compound containing lithium; and a compound represented by general formula (2)

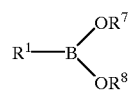

(2)

(wherein $R^1$ has the same meaning as defined above, $R^7$ and $R^8$, which may be the same or different, each represent an alkyl group which may have a substituent group, an alkenyl group which may have a substituent group, an aryl group which may have a substituent group, an aralkyl group which may have a substituent group, or an alicyclic group which may have a substituent group, or $R^7$ and $R^8$ combine with each other together with the boron atom and oxygen atoms to which they are attached to form a cyclic structure); and a compound represented by general formula (3)

$$R^2-Y \quad (3)$$

(wherein $R^2$ has the same meaning as defined above and Y represents a hydrogen atom or a halogen atom) to produce a borate metal salt represented by general formula (4)

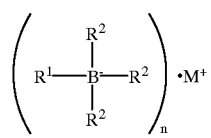

(4)

(wherein $R^1$ and $R^2$ have the same meanings as defined above, M is lithium or magnesium and n is 1 when M is lithium or 2 when M is magnesium), and a second step of adding to the borate metal salt an onium halide represented by general formula (5)

$$Z^+ \cdot X^- \quad (5)$$

(wherein $Z^+$ has the same meaning as defined above and $X^-$ represents a halide anion) to effect ion exchange reaction.

2. The method of producing a boron-based compound represented by general formula (1) as claimed in claim 1, wherein the onium halide represented by the general formula (5) is an ammonium halide represented by general formula (6)

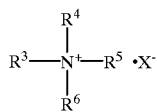

(wherein X⁻ has the same meaning as defined above and $R^3$, $R^4$, $R^5$, and $R^6$ independently represent an alkyl group which may have a substituent group, an aryl group which may have a substituent group, an aralkyl group which may have a substituent group, or an alicyclic group which may have a substituent group).

3. The method of producing a boron-based compound represented by the general formula (1) as claim 1 or 2, wherein in the first step, lithium, magnesium or the compound containing lithium and the compound represented by the general formula (3) are reacted in a solvent and then the compound represented by the general formula (2) is added to obtain the borate metal salt represented by the general formula (4).

4. The method of producing a boron-based compound represented by the general formula (1) as claim 1 or 2, wherein in the first step, a product obtained by reacting lithium, magnesium or the compound containing lithium and the compound represented by the general formula (3) in a solvent is added to the compound represented by the general formula (2) to obtain the borate metal salt represented by the general formula (4).

5. The method of producing a boron-based compound represented by the general formula (1) as claim 1 or 2, wherein in the first step, lithium, magnesium or the compound containing lithium and the compound represented by the general formula (3) are reacted in a solvent in the presence of the compound represented by the general formula (2) to obtain the borate metal salt represented by the general formula (4).

6. The method of producing a boron-based compound represented by the general formula (1) as claimed in claim 1 or 2, wherein in the first step, lithium or magnesium is used and a halide is used as the compound represented by the general formula (3).

7. The method of producing a boron-based compound represented by the general formula (1) as claimed in claim 1 or 2, wherein in the first step, an organic lithium compound is used and a halide is used as the compound represented by the general formula (3).

8. The method of producing a boron-based compound represented by the general formula (1) as claimed in claim 3, wherein in the first step, lithium or magnesium is used and a halide is used as the compound represented by the general formula (3).

9. The method of producing a boron-based compound represented by the general formula (1) as claimed in claim 4, wherein in the first step, lithium or magnesium is used and a halide is used as the compound represented by the general formula (3).

10. The method of producing a boron-based compound represented by the general formula (1) as claimed in claim 5, wherein in the first step, lithium or magnesium is used and a halide is used as the compound represented by the general formula (3).

11. The method of producing a boron-based compound represented by the general formula (1) as claimed in claim 3, wherein in the first step, an organic lithium compound is used and a halide is used as the compound represented by the general formula (3).

12. The method of producing a boron-based compound represented by the general formula (1) as claimed in claim 4, wherein in the first step, an organic lithium compound is used and a halide is used as the compound represented by the general formula (3).

13. The method of producing a boron-based compound represented by the general formula (1) as claimed in claim 5, wherein in the first step, an organic lithium compound is used and a halide is used as the compound represented by the general formula (3).

* * * * *